United States Patent [19]

Jones et al.

[11] Patent Number: 5,534,652
[45] Date of Patent: Jul. 9, 1996

[54] PREPARATION OF PLASTICIZER ESTERS FROM PHTHALIC ANHYDRIDE RESIDUE

[75] Inventors: Larry O. Jones, Baton Rouge, La.; Paul H. Daniels, League City, Tex.; Leonard G. Krauskopf; Konstantinos R. Rigopoulos, both of Baton Rouge, La.; Richard H. Schlosberg, Bridgewater, N.J.

[73] Assignee: Exxon Chemical Patents Inc. (ECPI), Linden, N.J.

[21] Appl. No.: 324,544

[22] Filed: Oct. 18, 1994

[51] Int. Cl.⁶ .................................................. C07C 67/08
[52] U.S. Cl. ................................................ 560/98; 560/99
[58] Field of Search ........................................ 560/98, 99

[56] References Cited

U.S. PATENT DOCUMENTS 5,214,157  5/1993  Healy et al. .................... 549/250
5,324,853  6/1994  Jones et al. ..................... 560/98

Primary Examiner—José G. Dees
Assistant Examiner—Samuel Barts
Attorney, Agent, or Firm—Richard D. Jordan

[57] ABSTRACT

A process for the formation of esters from at least one phthalic anhydride residue stream produced from the vapor phase oxidation of o-xylene, naphthalene and/or the like which comprises: (a) adding a phthalic anhydride residue stream and a mono-alcohol to a reaction vessel to form a reaction mixture; and (b) heating the reaction mixture and maintaining a pressure sufficient to obtain boiling of the reaction mixture thereby converting any acid and/or anhydride components of the phthalic anhydride residue stream to an ester.

16 Claims, 1 Drawing Sheet

PREPARATION OF PLASTICIZER ESTERS FROM PHTHALIC ANHYDRIDE RESIDUE

The present invention relates primarily to a system and process for producing mixed plasticizer esters, such as phthalates, adipates and trimellitates, by reacting alcohols with a phthalic anhydride residue stream produced from the vapor phase oxidation of o-xylene, naphthalene and/or the like. These esters are preferably used as low grade plasticizers, plasticizer extenders, lubricants, or greases.

BACKGROUND OF THE INVENTION

Phthalic anhydride is an intermediate compound used principally in the manufacture of plasticizers, polyesters and alkyd resins. The plasticizers are of two types: diesters of a monohydric alcohol, e.g., dibutyl phthalate, and mixed esters of two monohydric alcohols. Plasticizers can be made from the reaction of a variety of acids and/or anhydrides with an alcohol or a mixture of alcohols. It would be extremely desirable to find an inexpensive source of acids and/or anhydrides for use in forming plasticizers.

The present inventors have discovered a suitable source of acids and/or anhydrides for use in synthesizing plasticizer esters. This source is the phthalic anhydride residue from the various distillation or fractionation columns used in the finishing section of conventional phthalic anhydride processes. These distillation columns provide a readily available source of phthalic anhydride, benzoic acid, maleic anhydride, citraconic anhydride, etc. which can be reacted with an alcohol or a mixture of alcohols to form a mixture of esters.

Phthalic anhydride is typically produced from raw materials such as orthoxylene (o-xylene), petroleum naphthalene, and coal-tar naphthalene. The price of these raw materials and, as a direct result, the price of phthalic anhydride have fluctuated greatly depending upon supply and demand. Because the cost of the raw materials is a major factor in the price of phthalic anhydride it is of great importance that any system used to produce phthalic anhydride capture as much of the resultant product as possible.

Phthalic anhydride can be successfully produced from any of a number of processes, i.e., (1) air oxidation of o-xylene in fixed-bed reactors, (2) air oxidation of petroleum or coal tar naphthalene in fixed-bed reactors, (3) fluid bed oxidation of o-xylene, (4) fluid bed oxidation of petroleum or coal tar naphthalene, and (5) liquid phase oxidation of o-xylene.

The general process scheme for the various vapor phase routes is to mix the hydrocarbon feed (in the vapor form) with compressed air and to feed the mixture to fixed-bed reactors which contain tubes packed with catalysts, e.g., vanadium oxide and titanium dioxide coated on an inert, nonporous carrier. After the product stream exits either the fixed-bed or fluid bed reactors, it is cooled to cause the phthalic anhydride to condense. This allows separation of the phthalic anhydride from the gas stream. The crude phthalic anhydride is usually heat-treated in a decomposer, and in some cases chemical treatments are added to the decomposer. The purpose of the heat treatment is to dehydrate any phthalic acid in the crude to phthalic anhydride, to boil off materials such as water, and to form either condensation or volatile products from the various impurities so that the subsequent product purification by distillation is simplified. After distillation, the pure molten product may be solidified, flaked, bagged, and stored in a warehouse. Alternatively, the molten product may be pumped into large storage tanks and then into tank cars for shipment.

Distillation typically occurs in two fractionation columns or towers connected in series, wherein the bottoms stream from the first fractionation column is fed into the second fractionation column wherein substantially pure phthalic anhydride is taken overhead therefrom. The overhead stream from the first fractionation column is typically a light residue which comprises phthalic anhydride, maleic anhydride, benzoic acid and citraconic anhydride. The bottoms stream from the second fractionation column is typically a heavy residue (HOYS) which comprises phthalic anhydride and a mixture of compounds such as pryomellitic di-anhydride, anthraquinone, anthraquinone carboxylic acid, trimelletic acid or anhydride, biphthalyl, and various unknown components. Typically, the residue has an acidity per gram about equivalent to phthalic anhydride. Optionally, the bottoms from the second tower may be fed to a concentrating or residue drum where phthalic anhydride is recovered overhead and the distillation bottoms (i.e., heavies or HOYS) are concentrated into a residue stream.

The light residue from the first fractionation column and the heavy residue from the second fractionation column can, optionally, be disposed of by mixing together and then burning. This provides various environmental disposal problems. It also involves the wasting of commercially valuable products such as phthalic anhydride, maleic anhydride, benzoic acid, citraconic anhydride, and pryomellitic di-anhydride.

The present inventors have discovered a process which disposes the phthalic anhydride in an environmentally acceptable way and which avoids the increased cost associated with burning the residue or disposing by other means. The process of the present invention is capable of utilizing the light and heavy phthalic anhydride residue to synthesize mixed esters which are useful as low grade plasticizers, plasticizer extenders, lubricants, and/or greases. Thus, taking what are normally considered waste streams from the fractionation columns of the finishing section of a typical phthalic anhydride synthesis process and creating useful, saleable products by reaction of the streams with suitable alcohols in the presence of a catalyst.

The present invention also provides many additional advantages which shall become apparent as described below.

SUMMARY OF THE INVENTION

A process for the formation of esters from at least one phthalic anhydride residue stream produced from the vapor phase oxidation of o-xylene, naphthalene and/or the like. The esterification process comprises: (a) adding a phthalic anhydride residue stream and a mono-alcohol to a reaction vessel to form a reaction mixture; and (b) heating the reaction mixture to a temperature in the range between about 150° to 280° C., preferably between about 180° to about 260° C., and maintaining a pressure sufficient to obtain boiling of the reaction mixture thereby causing esterification of the reactants.

The phthalic anhydride residue stream is preferably an overhead phthalic anhydride residue stream from a first fractionation column and/or a bottoms phthalic anhydride residue stream from a second fractionation column of the finishing section of such vapor phase oxidation of o-xylene, naphthalene and/or the like. Optionally, the phthalic anhydride residue stream comprise the overhead phthalic anhydride residue stream from the first fractionation column and/or a bottoms phthalic anhydride residue stream from a concentrating or residue drum which is connected to the bottoms stream of the second fractionation tower.

The overhead phthalic anhydride residue stream from the first fractionation column typically comprises at least one component selected from the group consisting of: phthalic anhydride, benzoic acid and citraconic anhydride. The ester formed from the esterification of the overhead stream is useful as a plasticizer extender.

The bottoms phthalic anhydride residue stream from the second fractionation column typically comprises at least one component selected from the group consisting of: phthalic anhydride, pryomellitic di-anhydride, anthraquinone, anthraquinone carboxylic acid, trimelletic acid anhydride and biphthalyl. The ester formed from the esterification of the bottoms stream is useful as either a low grade plasticizer, a plasticizer extender, a lubricant or grease.

The process according to the present invention preferably comprises the addition of a catalyst to the reaction vessel such that the respective phthalic anhydride residue stream and the alcohol is catalytically converted to an ester. The catalyst is preferably selected from the group consisting of titanium, zirconium and tin-based catalysts. The catalyst may also be an acid catalyst, such as $H_2SO_4$, para-toluene sulfonic acid (p-TSA) and the like.

This process may comprise the following additional steps: addition of adsorbents such as alumina, silica gel, activated carbon, clay and/or filter aid to the ester mixture; addition of base to neutralize any residual organic or inorganic acids; filtration of solids from the ester mixture containing the bulk of the excess reagent (i.e., acid or alcohol) used in the esterification process; removal of the excess reagent from the ester mixture by steam and/or nitrogen stripping under vacuum and recycling of the excess reagent to the reaction vessel; and removing any residual solids from the stripped ester by means of secondary filtration.

In catalytic reactions, the neutralization step may also include the addition of water to hydrolyze the catalyst and, optionally, the addition of activated carbon for color removal. Further, the base may be added as a solution with the water. When hydrolysis occurs the process typically includes the following additional step, i.e., removal of the water used in the hydrolysis step by settling and/or by means of flashing. Optionally, clay or other adsorbent addition may follow water removal.

Other and further objectives, advantages and features of the present invention will be understood by reference to the following specification in conjunction with the annexed drawing.

DESCRIPTION OF THE PREFERRED EMBODIMENT

Figure 1:
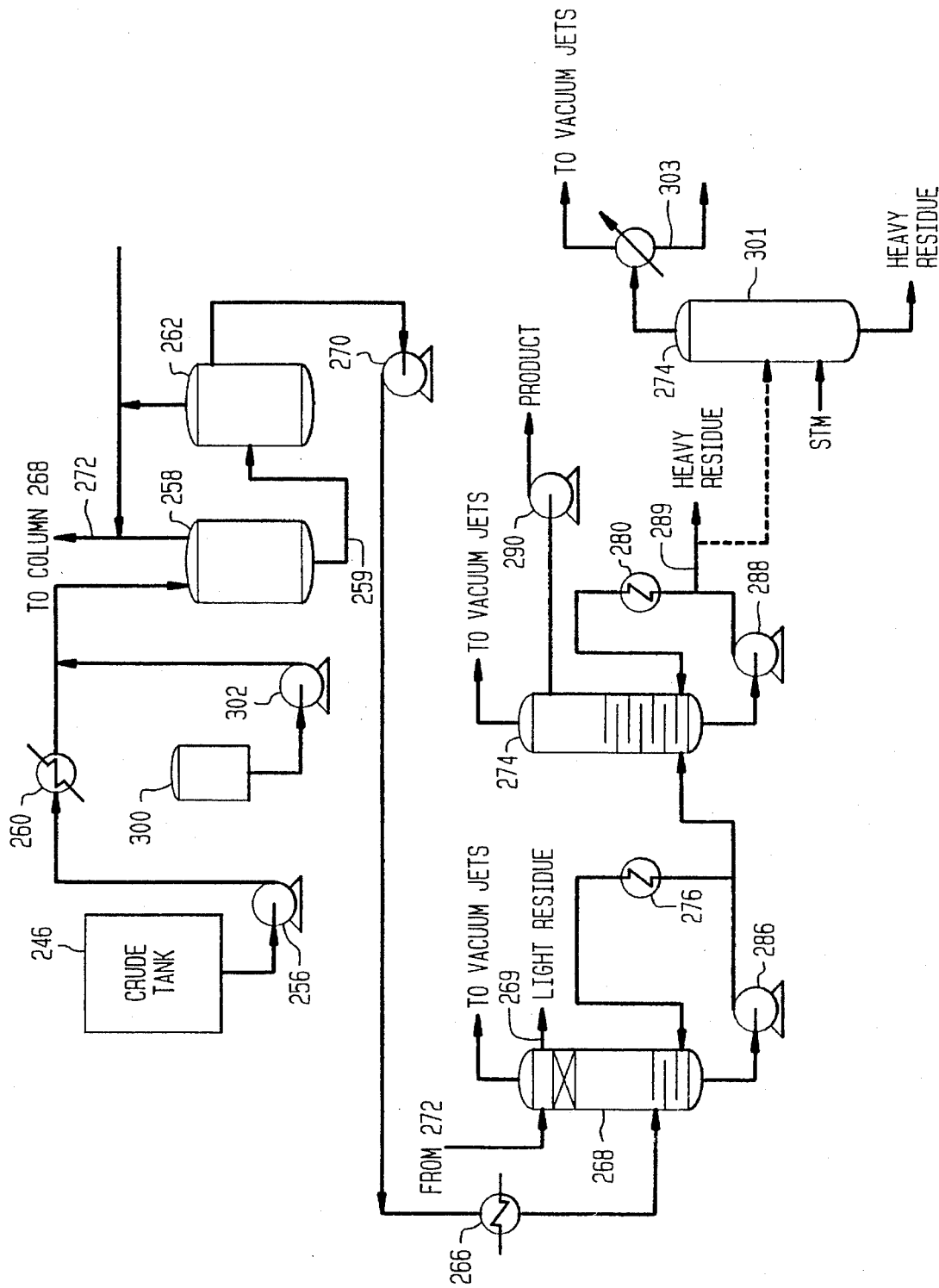
FIGURE 1 is a schematic flow chart depicting the finishing section of the vapor-phase system for the oxidation of phthalic anhydride from o-xylene according to the present invention.

The present invention is specifically directed to a process wherein the light phthalic anhydride residue from the overhead of the first fractionation column and/or the heavy phthalic anhydride residue from the bottoms of the second fractionation column, or, optionally, heavy phthalic anhydride residue from the bottoms of a residue drum which is connected to the bottoms stream of the second fractionation column, of the finishing section of a catalytic air oxidation process for synthesizing phthalic anhydride is reacted with at least one alcohol in the presence of a catalyst at elevated temperatures, thereby producing a mixed ester product which is useful as a low grade plasticizer, plasticizer extender, lubricant and/or grease.

This process includes the following steps:

a. esterification of a light and/or heavy phthalic anhydride residue, the light and/or heavy phthalic anhydride residue being derived from the fractionation columns of the finishing section of a catalytic air oxidation process for synthesizing phthalic anhydride, with excess alcohols and an esterification catalyst at a temperature in the range between about 150° to 280° C., preferably between about 180° to about 260° C., and maintaining a pressure sufficient to obtain boiling of the reaction mixture thereby causing the esterification of the light and/or heavy phthalic anhydride residue;

b. addition of adsorbents such as alumina, silica gel, activated carbon, clay and/or filter aid to the reaction mixture following esterification before further treatment, but in certain cases clay treatment may occur later in the process following either flash drying or steam or nitrogen stripping and in still other cases the clay may be eliminated from the process altogether;

c. addition of water and base to simultaneously neutralize the residual organic acids and hydrolyze the catalyst and, optionally, addition of activated carbon during hydrolysis;

d. removal of the water used in the hydrolysis step by heat and vacuum in a flash step, or removal of water by settling and decanting;

e. filtration of solids from the ester mixture containing the bulk of the excess alcohol used in the esterification reaction;

f. removal of excess alcohol by steam stripping or any other distillation method and recycling of the alcohol to the reaction vessel; and g. removing any residual solids from the stripped ester in a final filtration.

The preferred reactants used in these esterification processes are set forth below.

ESTERIFICATION CATALYSTS

Typical esterification catalysts are titanium, zirconium and tin catalysts such as titanium, zirconium and tin alcoholates, carboxylates and chelates. See U.S. Pat. Nos. 3,056,818 (Werber) which issued on Oct. 2, 1962, and 5,324,853 (Jones et al.), which issued on Jun. 28, 1994, and which are incorporated herein by reference.

Selected acid catalysts may also be used in this esterification process. Some examples of acid catalysts are: sulfuric acid, benzene sulfonic acid, p-toluene sulfonic acid, naphthalene sulfonic acid, aluminum sulfate, aluminum powder, normal decylbenzene sulfonic acid, normal dodecylbenzene sulfonic acid, normal nonylbenzene sulfonic acid, normal octylbenzene sulfonic acid, normal heptylbenzene sulfonic acid, normal hexylbenzene sulfonic acid, normal tridecylbenzene sulfonic acid, normal tetradecylbenzene sulfonic acid, normal dodecane sulfonic acid, normal tridecane sulfonic acid, normal tetradecane sulfonic acid, normal pentadecane sulfonic acid, normal hexadecane sulfonic acid, normal heptadecane sulfonic acid, normal octadecane sulfonic acid, normal nonadecane sulfonic acid, normal eicosane sulfonic acid, 3-methyldodecane sulfonic acid, 3-methyl-5ethyldecane sulfonic acid, 3-methyldecylbenzene sulfonic acid, 4-ethyloctylbenzene sulfonic acid, phosphoric acid, aromatic phosphonic acids (e.g., organic disulfonic acids, 1,2-ethanedisulfonic acid, 1,3-propanedisulfonic acid, m-benzene disulfonic acid, 2,5-, 2,6-, or 2,7-naphthalene disulfonic acids or mixtures of these isomers, and 3,5-o-xylenedisulfonic acid), acidic formalite resins prepared by reacting an aromatic hydrocarbon, an aldehyde, and sulfuric acid, methane disulfonic acid, methane trisulfonic acid, hydrochloric acid, perfluorinated resin sulfonic acid, acidic ion exchange resins, chlorosulfonic acid, thionyl chloride, boron trifluoride, dihydroxy fluoride, dihydroxy fluoboric acid, and silicon tetrafluoride.

ALCOHOLS

Among the alcohols which can be reacted with acids and anhydrides contained within the light and heavy phthalic anhydride residue streams are, by way of example, most primary and secondary $C_1$–$C_{30}$ monohydric, substituted or unsubstituted alkanols and alkenols, such as, methanol, ethanol, chloroethanol, cyanoethanol, ethoxy-ethanol, phenylethanol, n-propanol, 2-chloropropanol-1, 3-bromo-propanol-1, 2,2-dichloropropanol-1, isopropanol, propanol-2, 2-nitrobutanol-1, 2-nitrobutanol-1, 2-methylpentanol-1, 2-methyl pentanol-3, the primary and secondary octanols, n-dodecanol, 6-dodecanol, lauryl, myristyl, stearyl, 2-propenol-1, 2-butenol-1, 3-pentenol-1, ethylene glycol, trimethylene glycol, tetramethylene glycol, pentamethylene glycol, glycerol, 1,4-butanediol, neopentyl glycol, trimethylol propane, trimethylol ethane, trimethylol methane, mono and technical grade (i.e., 88% mono, 10% di and 1–2% tri) pentaerythritol, decane-1,10-diol, pentadecane-1,15-diol, pentacosane-1,25-diol, 2,4-hexadiene-1,6-diol, 2,4-octadiene-1,8-diol, and aromatic alcohols such as benzyl alcohol, o-, m- and p-methoxy alcohol, o-, m- and p-nitrobenzyl alcohol, o-, m- and p-methyl benzyl alcohol, phenyl ethyl alcohol, triphenyl ethyl alcohol, o-, m- and p-benzyl benzyl alcohol, alpha-naphthylethyl alcohol, beta-naphthyl ethyl alcohol, naphthylene-1,2-diethyl alcohol, phenylene-1,3,5-triethyl alcohol, and phenylene-1,4-dioctyl alcohols. This includes higher Guerbet alcohols which are beta carbon branched dimer alcohols having ten to twenty-six carbon atoms.

The alcohols may be obtained from various streams, i.e., mixed secondary alcohols from methyl ethyl ketone (MEK) process, and distillation bottoms from the recycle alcohol distillation (about 50% alcohol and 50% ethers).

The present invention can best be described by referring to FIGURE 1 which is a basic flow chart of the finishing section of the vapor-phase oxidation system used herein.

The crude phthalic anhydride from the oxidation section is preferably stored in tank 246 disposed upstream of the finishing section. Tank 246 is heated with steam to maintain the crude phthalic anhydride in a molten state.

Optionally, $Na_2CO_3$ can be added to the system in order to treat the crude phthalic anhydride. $Na_2CO_3$ has a beneficial effect on product quality. A solution of $Na_2CO_3$ in water can be prepared in drum 300 and meter-pumped upstream of decomposer 258.

The crude phthalic anhydride from tank 246 is heated as it passes through preheater 260 before it enters decomposer vessel 258. The bottoms from decomposer vessel 258 are sent to decomposer vessel 262 via conduit 259. Crude phthalic anhydride from decomposer vessel 262 is then pumped through cooler 266 to light ends fractionation column 268 (i.e., first distillation tower) via pump 270.

The vapor generated from decomposer vessels 258 and 262 is piped via steam-traced conduit 272 directly to the top portion of light ends fractionation column or first distillation tower 268.

The fractionation segment of the finishing section consists of first (topping or light ends) fractionation column or distillation tower 268 and second (tailing or product) fractionation column or distillation tower 274, with their respective reboilers, i.e., column 268 is connected to reboiler 276 and column 274 is connected to reboiler 280. Fully spared steam jet ejectors (not shown) are also provided on the top of fractionation columns 268 and 274 to provide column vacuum.

The reboilers are suppressed-vaporization pump-through types with pumps 286 and 288, respectively, which also pump out the bottom products from the associated fractionation column. Finished product from second fractionation column 274 is pumped via pump 290 to product tankage, not shown.

The overhead phthalic anhydride residue from first fractionation column 268 typically comprises about 50–85% phthalic anhydride, 5–25% maleic anhydride, 5–25% benzoic acid, and 0–2% citraconic anhydride. The bottoms phthalic anhydride residue from second fractionation column 274 exist via conduit 289, and typically comprises about 25–70% phthalic anhydride, 110% pyromellitic dianhydride, 1–5% anthraquinone, 110% anthraquinone carboxylic acid, 30–50% of unknown heavies fraction, including tri-melletic acid anhydride and biphthalyl. The acid number (i.e., milliequivalents per gram of sample) of the unknown heavies fraction is preferably between about 600 to 760. The acid number for phthalic anhydride is 758.

Optionally, the heavy phthalic anhydride residue from conduit 289 may be separated further by delivering the residue to concentrating or residue drum 301 wherein phthalic anhydride is taken overhead and either returned to decomposer vessel 258 via conduit 303 or sent to vacuum jets. The bottoms from residue drum 301 contain heavy phthalic anhydride residue (HOYS).

EXAMPLE 1

Mixed plasticizer esters were synthesized from the catalytic reaction of isodecyl alcohol and a phthalic anhydride residue taken from the bottoms of the second fractionation column in the finishing section of an existing phthalic anhydride plant using vapor phase oxidation of o-xylene.

780 grams of isodecyl alcohol, 281 grams of a phthalic anhydride residue obtained from the bottoms of a second fractionation column and 0.76 grams of a triisopropyl titanate catalyst were added to a reaction vessel and heated to 220° C. Reactor pressure was gradually reduced from 600 torr to 190 torr as the reaction progressed. Progress of the reaction was monitored by the amount of water that evolved. In this example, conversion based on residue as phthalic anhydride was 97.1%. The properties of the resulting product after neutralization, water removal and alcohol removal are set forth below in Table 1:

TABLE 1

| | |
|---|---|
| Specific Gravity @ 20° C. | 0.9752 |
| Pt—Co Color | dark |
| Acidity, Wt. % Phthalic Acid | 0.5 |
| Water Content, Wt. % | 0.06 |

EXAMPLE 2

Mixed plasticizer esters where synthesized from the catalytic reaction of isodecyl alcohol and a phthalic anhydride residue from the overhead of the first fractionation column in the finishing section of an existing phthalic anhydride plant using vapor phase oxidation of o-xylene.

800 grams of isodecyl alcohol, 313 grams of a phthalic anhydride residue obtained from the overhead of a first fractionation column and 0.9 grams of a tetraisopropyl titanate catalyst were added to a reaction vessel and heated to 220° C. Reactor pressure was gradually reduced from 600 torr to 140 torr as the reaction progressed. Progress of the reaction was monitored by the amount of water that evolved. In this example, conversion based on residue as phthalic anhydride was 99.9%. The properties of the resulting product are set forth below in Table 2:

TABLE 2

| | |
|---|---|
| Specific Gravity @ 20° C. | 0.9636 |
| Pt—Co Color | 115 |
| Acidity, Wt. % Phthalic Acid | 0.003 |
| Water Content, Wt. % | 0.04 |

EXAMPLE 3

The performance properties (i.e., modulus, tensile and elongation, plasticizer compatibility and plastisol (viscosity)) of the products from Examples 1 and 2 above were compared against a commercial diisodecyl phthalate (DIDP) sample all of which were incorporated in a standard polyvinylchloride (PVC) formula. The results of the comparison are set forth below in Tables 3 and 4.

TABLE 3

(Plasticizer in PVC Plastisols)

| Sample No. | Geon 121 (PVC) | Jayflex (DIDP) | Ex. 1 | Ex. 2 | Mark 7101 (Heat Stab.) |
|---|---|---|---|---|---|
| 1 | 100 | 0 | 70 | 0 | 2 |
| 2 | 100 | 35 | 35 | 0 | 2 |
| 3 | 100 | 63 | 7 | 0 | 2 |
| 4 | 100 | 0 | 0 | 70 | 2 |
| 5 | 100 | 35 | 0 | 35 | 2 |
| 6 | 100 | 63 | 0 | 7 | 2 |
| 7 | 100 | 70 | 0 | 0 | 2 |

The test protocol involved measuring the initial and 24 hours Brookfield (low shear) viscosities. Fused 0.040 inches (0.0157 cm) plastisol samples at 350° F. (176.7° C). Measured modulus, tensile and elongation values for die cut specimens from these samples.

TABLE 4

(Performance Properties)

| Properties | 1 | 2 | 3 | 4 | 5 | 6 | 7 |
|---|---|---|---|---|---|---|---|
| Brookfield Viscosity | | | | | | | |
| Initial | | | | | | | |
| 3 rpm | 7250 | 6250 | 3150 | 3200 | 2400 | 3200 | 3200 |
| 30 rpm | 6700 | 5300 | 3150 | 2580 | 2280 | 2800 | 2880 |
| 24 Hour | | | | | | | |
| 3 rpm | 7750 | 5500 | 3250 | 3300 | 2550 | 2950 | 3300 |
| 30 rpm | 7000 | 5200 | 3250 | 2800 | 2500 | 2900 | 3050 |

TABLE 4-continued (Performance Properties)

| Properties | 1 | 2 | 3 | 4 | 5 | 6 | 7 |
|---|---|---|---|---|---|---|---|
| Mechanical Properties | | | | | | | |
| Tensile Strength (psi) | 2220 | 2380 | 2380 | 2400 | 2380 | 2350 | 2480 |
| std. dev. | 186 | 301 | 165 | 91 | 123 | 158 | 70 |
| 100% Modulus, PSI | 1240 | 1130 | 1042 | 1000 | 1049 | 1080 | 1080 |
| std. dev. | 20 | 22 | 31 | 23 | 20 | 22 | 21 |
| Ultimate Elong. % | 305 | 368 | 387 | 412 | 388 | 384 | 400 |
| std. dev. | 41 | 64 | 45 | 33 | 35 | 37 | 25 |

The above samples 1–7 where aged at 70° C. and 100% relative humidity for between 1–21 days to determine plasticizer compatibility. The results are set forth below in Table 5:

TABLE 5

(Plasticizer Compatibility)

| Time | 1 | 2 | 3 | 4 | 5 | 6 | 7 |
|---|---|---|---|---|---|---|---|
| 1 day | ok | ok | ok | ok | ok | ok | ok |
| 3 days | ok | ok | ok | ok | ok | ok | ok |
| 7 days | ok | ok | ok | ok | ok | ok | ok |
| 14 days | s | vs | ok | ok | ok | ok | ok |
| 21 days | vs | ok | ok | ok | ok | ok | ok | ok denotes no incompatibility.
s denotes slight incompatibility.
vs denotes very slight incompatibility.

In summary, the di(isodecyl)phthalate made from the phthalic anhydride residue taken from the overhead of the first fractionation column (Example 2) provides performance properties in polyvinylchloride plastisols that are equivalent to those of commercial grade di(isodecyl)phthalate (DIDP) plasticizers. The equivalent sample made from the bottoms of the second fractionation column (Example 1) would appear to be limited to use as a plasticizer extender, rather than 0 as a primary plasticizer. It was exceptionally high in color, specific gravity and acidity. In polyvinylchloride plastisols it produced high viscosities and indicated limited compatibility. The tensile properties of the polyvinylchloride samples, however, were similar to the polyvinylchloride made with commercial grade DIDP plasticizers (sample no. 7 in Table 3).

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A process for the formation of mixed esters from at least one light phthalic anhydride residue stream produced from the vapor phase oxidation of o-xylene and/or naphthalene having an oxidation section and finishing section, wherein said light phthalic anhydride residue stream comprises at least two compounds selected from the group consisting of: phthalic anhydride, maleic anhydride, benzoic acid and citraconic acid, said process comprising:

a. adding said light phthalic anhydride residue taken from the overhead from a first fractionation column of said finishing section of said vapor phase oxidation of o-xylene, and/or naphthalene, and a mono-alcohol to a reaction vessel to form a reaction mixture; and b. heating said reaction mixture and maintaining a pressure sufficient to obtain boiling of said reaction mixture thereby converting any acid and/or anhydride components of said light phthalic anhydride residue stream to mixed esters.

2. The process according to claim 1 further comprising the addition of a catalyst to said reaction vessel such that said light phthalic anhydride residue stream and said alcohol is catalytically converted to said mixed esters.

3. The process according to claim 2 wherein said catalyst is selected from the group consisting of titanium, zirconium and tin-based catalysts.

4. The process according to claim 2 wherein said catalyst is an acid catalyst.

5. The process according to claim 1 further comprising at least one of the following additional steps:

c. removal of excess alcohol by nitrogen or steam stripping;

d. addition of an adsorbent selected from the group consisting of: alumina, silica gel, activated carbon, clay and/or filter aid to said ester mixture;

e. addition of base to neutralize any residual organic acids;

f. filtration of solids from said ester mixture containing the bulk of the excess alcohol used in the esterification process;

g. removal of said excess alcohol from said ester mixture by steam or nitrogen stripping and recycling of said excess alcohol to said reaction vessel; and h. removing any residual solids from the stripped ester by means of secondary filtration.

6. The process according to claim 2 further comprising adding water subsequent to heating step (b) so as to hydrolyze said catalyst.

7. The process according to claim 5 further comprising the following step:

i. removal of the water used in the hydrolysis step by settling and/or by means of flashing.

8. The process according to claim 5 wherein the addition of said adsorbent in step (d) may occur either before or after the stripping step (g).

9. The process according to claim 3 wherein said light phthalic anhydride residue stream comprises about 50–85% phthalic anhydride, 5–25% maleic anhydride, and 5–25% benzoic acid.

10. A process for the formation of mixed esters from at least one heavy phthalic anhydride residue stream produced from the vapor phase oxidation of o-xylene and/or naphthalene having an oxidation section and finishing section, wherein said heavy phthalic anhydride residue stream comprises at least two compounds selected from the group consisting of: phthalic anhydride, pryomellitic di-anhydride, anthraquinone carboxylic acid, trimelletic acid anhydride and biphthalyl, said process comprising:

a. adding said heavy phthalic anhydride residue taken from the bottoms of a second fractionation column of said finishing section of said vapor phase oxidation of o-xylene, and/or naphthalene, and a mono-alcohol to a reaction vessel to form a reaction mixture; and b. heating said reaction mixture and maintaining a pressure sufficient to obtain boiling of said reaction mixture thereby converting any acid and/or anhydride components of said heavy phthalic anhydride residue stream to said mixed esters.

11. The process according to claim 10 wherein said heavy phthalic anhydride residue stream is said bottoms phthalic anhydride residue stream from said second fractionation which has been separated further into a recycled phthalic anhydride stream and a second bottoms phthalic anhydride stream.

12. The process according to claim 10 wherein said oxidation section is capable of producing crude phthalic anhydride and said finishing section is capable of producing a substantially pure phthalic anhydride stream and said heavy phthalic anhydride residue stream.

13. The process according to claim 12 wherein said finishing section comprises a crude phthalic anhydride storage tank, at least one decomposer, a first fractionation column and said second fractionation column, wherein said heavy phthalic anhydride residue is taken from the bottoms of said second fractionation column.

14. The process according to claim 10 wherein said heavy phthalic anhydride residue stream comprises about 25–70% phthalic anhydride, 1–10% pryomellitic di-anhydride, 1–5% anthraquinone, and 1–10% anthraquinone carboxylic acid.

15. The process according to claim 1 wherein said oxidation section is capable of producing crude phthalic anhydride and said finishing section is capable of producing a substantially pure phthalic anhydride stream and said light phthalic anhydride residue stream.

16. The process according to claim 15 wherein said finishing section comprises a crude phthalic anhydride storage tank, at least one decomposer, said first fractionation column and a second fractionation column, wherein said light phthalic anhydride residue is taken from the overhead of said first fractionation column.

* * * * *